United States Patent
Bialkowski et al.

(10) Patent No.: US 10,231,685 B2
(45) Date of Patent: Mar. 19, 2019

(54) OPERATING AN X-RAY SYSTEM FOR EXAMINING AN OBJECT

(71) Applicant: SIEMENS HEALTHCARE GMBH, Erlangen (DE)

(72) Inventors: Jens Bialkowski, Neunkirchen am Brand (DE); Bernhard Geiger, Buckenhof (DE); Stefan Schneider, Erlangen (DE); Jan Steinbrener, Ingolstadt (DE)

(73) Assignee: Siemens Healthcare GmbH, Erlangen (DE)

(*) Notice: Subject to any disclaimer, the term of this patent is extended or adjusted under 35 U.S.C. 154(b) by 220 days.

(21) Appl. No.: 15/206,457

(22) Filed: Jul. 11, 2016

(65) Prior Publication Data

US 2017/0007194 A1    Jan. 12, 2017

(30) Foreign Application Priority Data

Jul. 9, 2015    (DE) .................. 10 2015 212 841

(51) Int. Cl.
*A61B 6/00* (2006.01)
*A61B 17/00* (2006.01)

(52) U.S. Cl.
CPC .............. *A61B 6/487* (2013.01); *A61B 6/469* (2013.01); *A61B 6/542* (2013.01); *A61B 6/461* (2013.01); *A61B 2017/00216* (2013.01)

(58) Field of Classification Search
CPC ......... A61B 6/542; A61B 6/487; A61B 6/469; A61B 6/461; A61B 2017/00216
See application file for complete search history.

(56) References Cited

U.S. PATENT DOCUMENTS

| 7,170,974 | B2 | 1/2007 | Groh et al. |
| 7,500,783 | B2 | 3/2009 | Kalender |
| 2006/0265307 | A1 | 11/2006 | Walker, Jr. |
| 2015/0023466 | A1* | 1/2015 | Melman ............... A61B 6/06 378/42 |
| 2015/0164440 | A1* | 6/2015 | Rackow ............ A61B 5/7485 600/427 |

FOREIGN PATENT DOCUMENTS

| DE | 10354899 A1 | 6/2005 |
| DE | 102005003225 A1 | 7/2006 |
| DE | 102006044783 A1 | 4/2008 |
| DE | 102013226242 A1 | 6/2015 |

* cited by examiner

*Primary Examiner* — Dani Fox
(74) *Attorney, Agent, or Firm* — Laurence Greenberg; Werner Stemer; Ralph Locher

(57) ABSTRACT

A method operates an x-ray system for examining an object. In order to optimize the operation of an x-ray system, in particular the dose regulation and/or the image processing, the following method steps are performed. Radiation is passed through the object to be examined and a number of fluoroscopic images of the object are generated. A relevant image region of a fluoroscopic image is selected by a user of the x-ray system. An image-based dose regulation of the radiation dose used for passing radiation through the object is carried out using the selected image region and/or image processing is carried out using the selected image region.

6 Claims, 2 Drawing Sheets

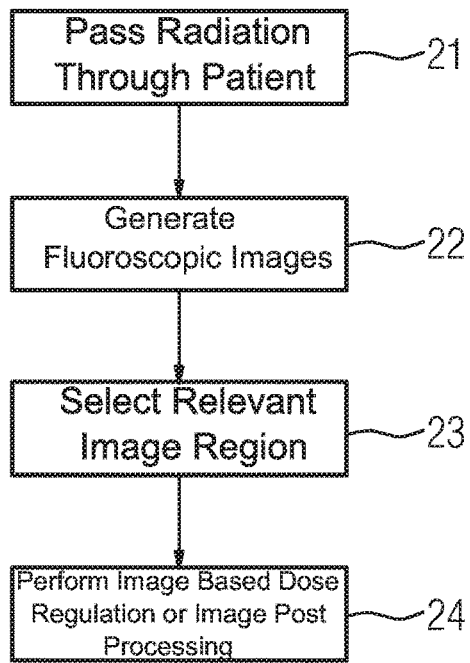
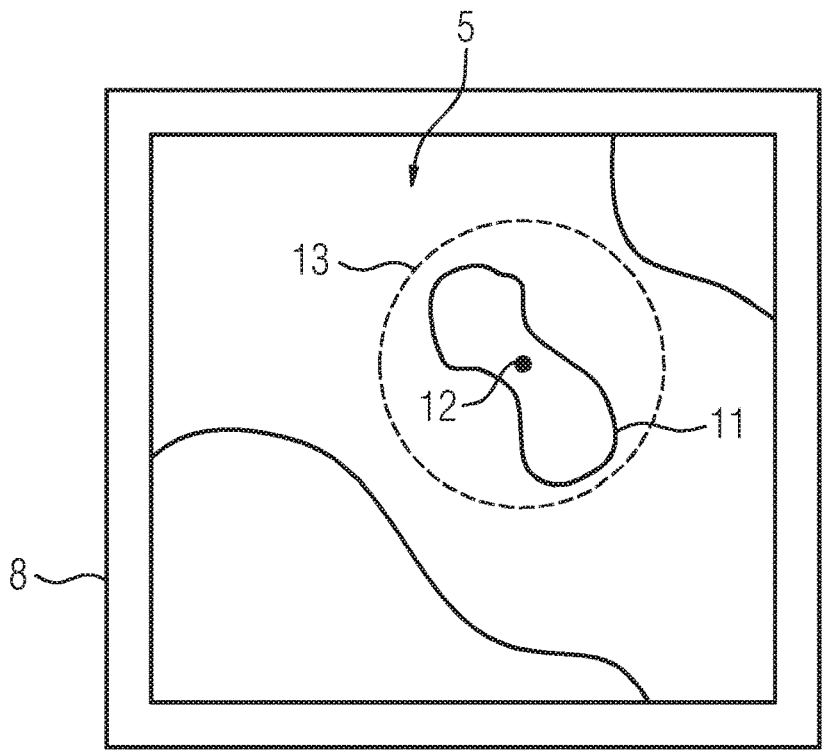

OPERATING AN X-RAY SYSTEM FOR EXAMINING AN OBJECT

CROSS-REFERENCE TO RELATED APPLICATION

This application claims the priority, under 35 U.S.C. § 119, of German application DE 10 2015 212 841.5, filed Jul. 9, 2015; the prior application is herewith incorporated by reference in its entirety.

BACKGROUND OF THE INVENTION

Field of the Invention

The present invention relates to a method for operating an x-ray system for examining an object. Moreover, the invention relates to such an x-ray system.

Published, non-prosecuted German patent applications DE 10 2013 226 242 A1 and DE 10 2006 044 783 A1 disclose methods for operating an x-ray system, in which the actual recording region of the medical x-ray recording, e.g. the start and end position in the case of CT imaging, is adjusted using an overview record. There, this recording region is adjusted by way of example by gestures of the user using a touch screen and/or cameras, or else by manual or automatic placement of a marking characterizing the recording region in the overview record. The actual x-ray recording is carried out following the adjustment of the recording region.

When examining an object with the aid of an x-ray system by generating fluoroscopic images, it is necessary, for various reasons, to distinguish between relevant and non-relevant image contents. Such a distinction is important, firstly, for adapting the radiation dose used to pass radiation through the object. Secondly, such a distinction is important to the image processing (image post-processing) of the fluoroscopic images.

The signal-to-noise ratio, with which an object situated in the beam path is imaged on a detector, is proportional to the transmitted radiation dose. The dose measured at the image receiver (x-ray detector) is therefore an indirect measure for the image quality and it is often predetermined as a setpoint variable for the dose regulation. In the case of systems without a detector-side ionization chamber, the radiation dose is usually calculated directly from the recorded image data (grayscale values). This is possible as the unprocessed image data are directly proportional to the absorbed radiation dose in digital x-ray systems.

Since the image data often also include regions without clinical relevance, e.g. direct radiation or metal objects, in addition to anatomical information, a decision needs to be made as to which image regions should be used for calculating the radiation dose. Advantageously, only those image regions which have relevant image contents are used for calculating the dose and, consequently, for regulating the radiation dose. The dose regulation is then based upon establishing the grayscale value in a set ROI (region of interest). Here, the intensity of the x-ray radiation is controlled in such a way that a constant mean value emerges.

Independently of a dose calculation, the image data of the fluoroscopic images must also be prepared in such a way that relevant information (e.g. clinically relevant information in the case of medical x-ray systems) is depicted in an ideal manner to the user. Here, a common problem is that the anatomical, potentially clinically relevant data also cover a large grayscale value range, which cannot be presented in an ideal manner to the user as a whole. Therefore, there must also be a selection of relevant image regions in the fluoroscopic image, even in the case of the image processing, which image regions are subsequently prepared for the user in an ideal manner.

Modern digital x-ray systems use one or more of the following methods for automatic image evaluation to distinguish between relevant image contents (e.g. clinically relevant anatomy) and other image contents.

In a first method, use is made of fixed measurement fields. Here, static image regions are set in relation to the image matrix, which image regions are evaluated for determining the radiation dose. The user can ensure correct dose regulation and image processing by virtue of setting the beam geometry in such a way that the part of interest of the object is imaged on this image region. The main disadvantage of this method consists of the fact that the user is restricted in terms of his workflow, particularly in respect of positioning the object and x-ray system.

In addition to this position-dependent object evaluation, a histogram regulation is applied as a second method. Here, relevant and non-relevant grayscale value regions are established dynamically with the aid of predefined rules using a histogram of the recorded image data. The goal is to ensure a position-independent object evaluation. The histogram regulation cannot ensure a correct evaluation of the image in specific clinical applications, e.g. lateral cervical spine or objects, e.g. very large metal implants. Then, there is a risk of the wrong image contents being considered relevant and therefore the dose regulation and/or image processing not being carried out correctly.

Manual regulation can be provided as a third method. Here, operating elements are offered to the user, with the aid of which the user can directly influence the parameters (current, voltage) of the x-ray apparatus in order to correct overexposure or underexposure on the part of the automatic image evaluation. Disadvantages of this method are the susceptibility to errors in the case of an incorrect interpretation of the user, the poor operability and the often non-ideal coupling to the image processing.

What should be noted overall is that, on account of the large scope of possible clinical applications and objects, it is not possible to exclude the case that an automated image evaluation with the above-described methods, including a possible manual correction, fails. This may occur both when establishing the relevant image contents for the dose regulation and during image processing. The possible consequences of an incorrect evaluation are, inter alia, an increased dose exposure for the object and operating staff and poor image quality due to underexposure or overexposure of the relevant structures or due to non-ideal preparation of the image data by the image processing.

SUMMARY OF THE INVENTION

Therefore, an object of the present invention is to optimize the operation of an x-ray system, in particular the dose regulation and/or the image processing.

The advantages and configurations explained below in conjunction with the method also apply analogously to the x-ray system according to the invention, and vice versa.

The method according to the invention for operating an x-ray system for examining an object includes the following steps: passing radiation through the object to be examined and generating a number of fluoroscopic images of the object, selecting at least one relevant image region of a fluoroscopic image, and carrying out an image-based dose regulation of the radiation dose used for passing radiation through the object using the selected image region and/or carrying out image processing using the selected image region. It is characterized in that the at least one relevant image region of the fluoroscopic image is selected by a user of the x-ray system.

Accordingly, the x-ray system according to the invention for examining an object contains an x-ray radiation source for passing radiation through the object to be examined, an x-ray detector for generating a number of fluoroscopic images of the object, a selection unit for selecting at least one relevant image region of a fluoroscopic image, and a dose regulation unit for carrying out an image-based dose regulation and/or an image processing unit. The x-ray system is characterized in that the selection unit is embodied for the at least one relevant image region of the fluoroscopic image to be selected by a user of the x-ray system.

What image regions count as relevant depends on the purpose of the examination. By way of example, in the case of clinical diagnostic systems, those image regions in which clinically relevant anatomy is imaged are considered relevant image regions.

If reference is made in general terms to selecting a relevant image region by the user, this selection can take place by marking image region boundaries in the simplest case. By way of example, a specific image region (ROI) can be marked by the user with the aid of a polygonal line. In a preferred embodiment of the invention, the image region is selected by selecting image content in a fluoroscopic image displayed on an image display instrument within the scope of characterizing, marking or determining a local structure as an ROI.

In a particularly preferred embodiment of the invention, only one point of the image content of interest, in particular of a local structure imaged in the fluoroscopic image, needs to be selected for this purpose. Then, this point forms the center of a predefined image region automatically generated by the x-ray system, which image region is determinable in terms of form and size.

The selection of the point can be carried out by touching a touch-sensitive image display instrument or in any other suitable manner by contact. In a preferred embodiment of the invention, there is a contactless selection of the point, preferably by applying an eye tracking method.

Marking image content of interest by defining an image region with the aid of a polygonal line or in a similar manner is preferably applied within the scope of the findings, while a touch system is advantageous in more dynamic applications, for example within the settings of the operating theater, or else the operation is carried out directly by the surgeon with the aid of the eye tracking method.

The dose regulation is carried out to generate ideal image data, in particular in view of contrast and brightness. Image processing is carried out to generate an optimized image of the object to be displayed to a user of the x-ray system. To this end, there is image processing of at least one region of at least one of the number of fluoroscopic images.

In accordance with the invention, carrying out the dose regulation or the image processing using the selected image region means that the dose regulation or the image processing is optimized for the selected image region. In other words, after selecting a specific relevant image region, there is dose regulation and/or image processing optimized for this image region. By way of example, such an optimization can take place by omitting other image regions or else by a different weighting of the various image regions in order to determine what influence an image region has on the result of the dose regulation or the image processing.

Consequently, an adaptation of the radiation dose or a specific manner of image processing automatically affects further image regions with comparable or similar image contents.

In accordance with a preferred embodiment of the invention, the effect of the optimization of the dose regulation or the image processing is extended to further image regions with comparable or similar image contents on the basis of a number of specific properties of the selected image region or, expressed differently, on the basis of defined similarity criteria. To this end, specific properties of the local structures are used to search for comparable structures in the overall image and to subsequently optimize these as well.

By way of example, these properties can be the local distribution of the grayscale values. Then, search criteria are e.g. minimum/maximum values, mean values, standard deviations, etc., wherein histogram-based comparisons are also possible. Comparable structures can also be determined on the basis of the two-dimensional structure thereof, for example by comparing the 2D spectra of the contained spatial frequencies. The search for comparable structures can also take place on the basis of the displayed form; by way of example, it is thus possible to distinguish anatomical forms (similar ribs, vertebrae, etc.) and artificial forms (e.g. implants). Other structure properties relate to the size of the local structure (the extent thereof in pixels), the belonging thereof to the skeleton as a primary structure, or using other properties such as contours and preferred directions visible in the image. It is likewise possible to determine comparable structures on the basis of changes over time, for example by using a 3D analysis of the spectra, the change of the grayscale values per unit time or the movement direction.

By way of the present invention, the user of the x-ray system is provided with an image-based option for optimizing the dose regulation and/or the image processing in a region of interest. The manual selection of relevant regions proposed by the invention is preferably carried out instead of an image evaluation carried out by a machine with a rule-based image region selection. The proposed manual selection can, however, also take place following such an automated image evaluation in order to be able to correct a failed image evaluation in the simplest possible manner.

In other words, the manual selection of a relevant image region proposed by the invention can replace the automatic image evaluation known from the prior art, for example by the three above-described methods, or else it can complement the automatic image evaluation by a manual pre selection of relevant image regions. In the latter case, the subsequent automated procedure need no longer relate to the entire fluoroscopic image, i.e. not all image regions of the fluoroscopic image. Instead, the manual pre selection deselects non-relevant regions which are not of interest a priori. The automatic image evaluation then only still takes place for the manually selected image regions, possibly in addition to the automatically co-selected image regions with similar image contents.

A number of advantages arise in relation to the methods known from the prior art. It is particularly advantageous that the application of the invention has no restrictions on the (clinical) workflow as a consequence as the method complements the already available automatic image evaluation methods, i.e. it can be offered and/or carried out in parallel with the other methods. A further substantial advantage lies in the simple, intuitive operability of the x-ray system which is complemented in terms of the functionality thereof in respect of the dose regulation and/or in respect of the image processing. The selection of the known image content in an image can be carried out intuitively and quickly, particularly if the selection is carried out by marking the center of a structure of interest and a predefined ROI.

A further substantial advantage lies in the avoidance of unnecessary radiation exposure of the object (patient) and operating and/or clinical staff. A one-time selection of the relevant object can prevent a repeated incorrect evaluation of the image in consecutive radiation sequences and therefore avoid unnecessary radiation (e.g. by underexposure or overexposure).

A fully automatic solution for finding the relevant image regions with the aid of the methods known from the prior art and described above is difficult, particularly in the case of dynamic imaging such as in the case of e.g. an operation. In a disadvantageous case, the automated dose regulation is then based on a clinically non-relevant image region, and so a body part with e.g. particularly high bone density is not depicted in an ideal manner. At the same time, the image processing can be based on a non-relevant image region such that the anatomical structures of most interest to the user are only depicted with a very weak contrast. By applying the present invention, it is possible in a particularly simple manner, for example by simply tapping the screen or else, in the case of applying the eye tracking method, by merely looking onto a local structure of particular interest, to achieve an optimized dose regulation and/or optimized image processing. In the used example, the very dense bone complex is imaged more clearly or the structure of interest is displayed with an ideal contrast enhancement.

The method according to the invention can be carried out in a computer-assisted manner. The device suitable for carrying out the method according to the invention can be substantially realized by providing a suitable computer program. To this end, a costly modification of the hardware is not necessarily required.

The present invention is applicable in x-ray systems of different types, but preferably in digital x-ray systems, particularly in digital 2D x-ray systems for clinical diagnostics or interventions.

Other features which are considered as characteristic for the invention are set forth in the appended claims.

Although the invention is illustrated and described herein as embodied in a operating an x-ray system for examining an object, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 2 is a flowchart of the method according to the invention; and

FIG. 3 is an illustration of a monitor with an image of a fluoroscopic image and the selection of an image region.

DETAILED DESCRIPTION OF THE INVENTION

Figure 1:
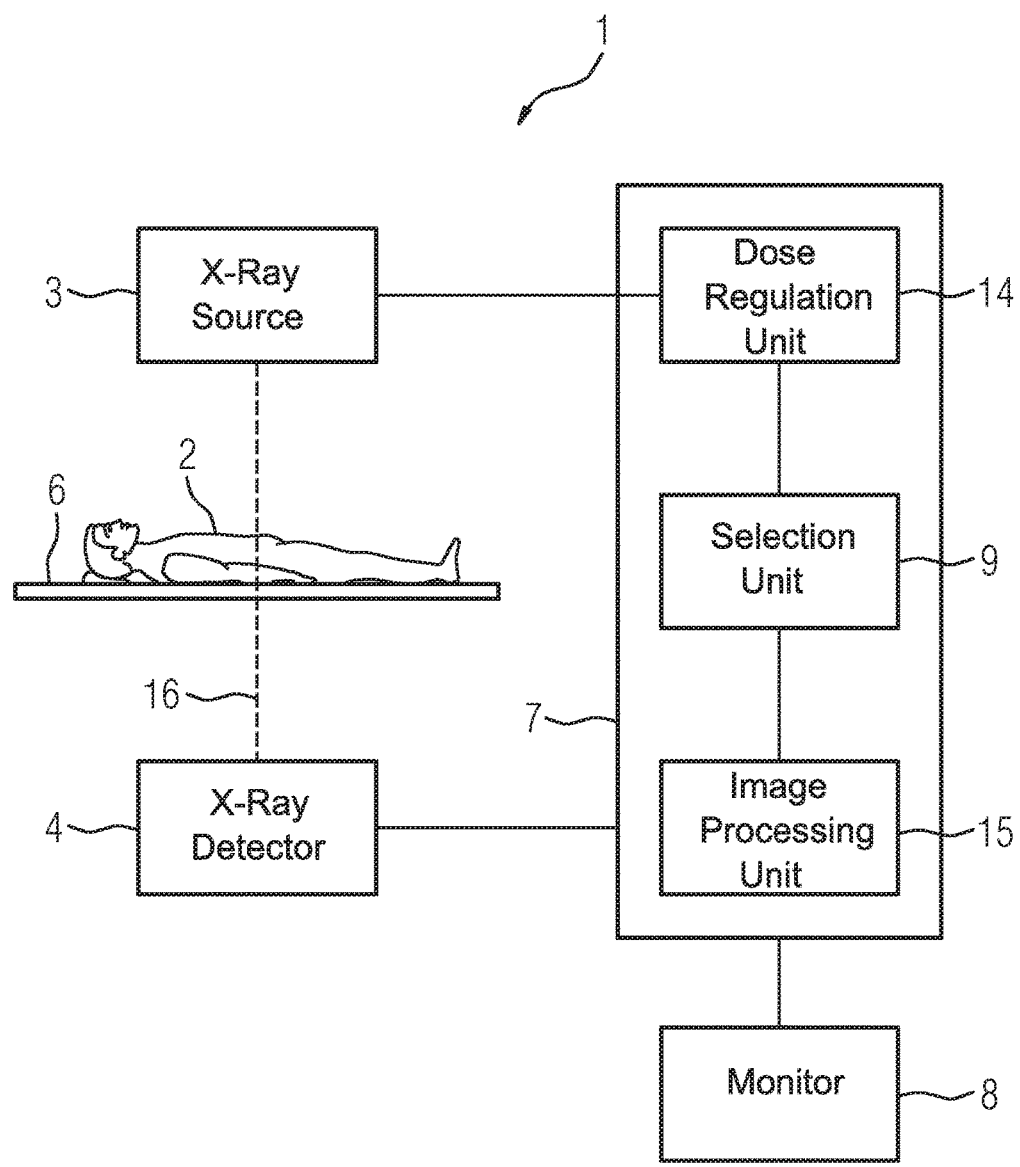
FIG. 1 is a simplified, schematic illustration of an x-ray system according to the invention.

All figures show the invention merely schematically and with its essential components. Here, the same reference signs correspond to elements with the same or a comparable function.

Referring now to the figures of the drawings in detail and first, particularly to FIG. 1 thereof, there is shown a digital 2D x-ray system 1 for examining a patient 2 and serving as an x-ray diagnostic system, as can be employed in the present invention. The x-ray system 1 contains, as is known, an x-ray radiation source (x-ray tube) 3 for passing (step 21) radiation through the patient 2 and an x-ray detector 4 for generating (step 22) a number of fluoroscopic images 5 of the patient 2. During the recordings, the patient 2 is situated on a patient-bearing table 6.

The x-ray detector 4 is connected to an evaluation apparatus 7. The evaluation apparatus 7 processes the measurement data detected by the x-ray detector 4 in order to obtain a suitable image display on a monitor 8 connected to the evaluation apparatus 7.

The evaluation apparatus 7 contains a selection unit 9 for selecting (step 23) a relevant image region of a fluoroscopic image 5 by a user of the x-ray system.

The invention proposes to provide the user of the x-ray system 1 with indirect control over an image-based dose regulation and/or image post-processing by virtue of the user marking image content of interest to him (ROI) in a representative image 5 which is displayed to him on the monitor 8 or any other suitable digital image display instrument.

This can be carried out in various ways, for example, like in the present case, by pressing a finger onto the monitor 8, which is embodied as a touch-screen monitor to this end. However, marking relevant image content can also be carried for example out by a mouse click or by a visual selection with the aid of an installed eye tracking system.

In order to simplify operation, it should not be mandatory for the user to mark the whole ROI by a polygonal line. Instead, it is also sufficient to mark the center of a predefined ROI with an adjustable size and form. In other words, the selection of the relevant image region, for example a local anatomical structure of interest, can be carried out by selecting specific image content, in this case e.g. by marking an image point 12 representing a bone 11.

In FIG. 3, such a point 12 is marked by a user within a displayed structure 11. Subsequently, a predefined ROI 13 is generated automatically by the selection unit 9, in this case in circular form.

The representative image, with the aid of which the selection is carried out, is preferably the live image 5 from the current fluoroscopic sequence. However, in this case, this can also be e.g. an LIH (last image hold) from the preceding fluoroscopic sequence.

As soon as image content 13 was selected, the dose regulation and/or the image post-processing is optimized for this region. By way of example, an optimization means that the histogram regulation is only carried out with those image data which are situated in the marked ROI 13.

The optimization relating to a specific image region after a selection of the ROI 13 can take place either for the dose regulation and the image processing or else in respect of only one of these two applications.

An optimization of the dose regulation is only active for the subsequently recorded images. An optimization of the image processing can be applied immediately to the already recorded images 5, in particular also in a retrospective manner. The user can decide whether or not he wishes to maintain the optimized parameters for further radiation sequences.

There subsequently the image-based dose regulation and/or image post-processing is performed using (step 24) the selected image region. Accordingly, the evaluation apparatus 7 contains a dose regulation unit 14 connected to the x-ray radiation source 3, for carrying out an image-based dose regulation for adapting the radiation dose of the x-ray radiation source 3, and also an image processing unit 15 for carrying out image post-processing of the fluoroscopic images 5 for generating ideal displays on the monitor 8.

Here, the dose regulation can be carried out according to a predetermined program on the basis of a grayscale value analysis of the selected relevant image region 13, for example by changing the tube voltage or by swiveling a variable attenuation element, arranged upstream of the x-ray tube, into the beam path 16.

The evaluation apparatus 7 is configured in such a way that it can carry out a method of the type explained above. It is particularly advantageous if the x-ray system 1 according to the invention contains a computer and a means for selecting a relevant image region 13 of a fluoroscopic image 5 by way of a user of the x-ray system 1 is carried out as a computer program or implemented by means of a computer program.

Although the invention is illustrated more closely and described in detail by the preferred exemplary embodiment, the invention is not restricted to the disclosed examples and other variations can be derived herefrom by a person skilled in the art without departing from the scope of protection of the invention.

The following is a summary list of reference numerals and the corresponding structure used in the above description of the invention:

1 X-ray system
2 Patient
3 X-ray radiation source
4 X-ray radiation detector
5 Fluoroscopic image
6 Patient-bearing table
7 Evaluation apparatus
8 Monitor
9 Evaluation unit
10 (unassigned)
11 Bones, local structure
12 Image point
13 ROI, selected image region
14 Dose regulation unit
15 Image processing unit
16 Beam path

The invention claimed is:

1. A method for operating an x-ray system for examining an object, which comprises the following steps of:
 passing radiation through the object to be examined;
 generating a number of fluoroscopic images of the object;
 selecting a relevant image region of a representative fluoroscopic image;
 carrying out an image-based dose regulation of a radiation dose used for passing radiation through the object using a selected relevant image region;
 carrying out image processing using the selected relevant image region;
 optimizing the dose regulation and the image processing for the selected relevant image region, the dose regulation being an image-based dose regulation optimized by a different weighting of various image sections of the selected relevant image region; and
 selecting the selected relevant image region of the fluoroscopic image via a user of the x-ray system.

2. The method according to claim 1, which further comprises selecting the selected relevant image region of the fluoroscopic image based on an image content in the fluoroscopic image displayed on an image display instrument.

3. The method according to claim 2, which further comprises selecting the image content by selecting a point of a local structure imaged in the fluoroscopic image, wherein the point forms a center of the selected relevant image region.

4. The method according to claim 3, which further comprises selecting the point by way of an eye tracking method.

5. The method according to claim 1, which further comprises automatically co-selecting further image regions on a basis of a number of specific properties of the selected relevant image region.

6. An x-ray system for examining an object, comprising:
 an x-ray radiation source for passing radiation through the object to be examined;
 an x-ray detector for generating a number of fluoroscopic images of the object;
 a selection unit for selecting a relevant image region of a representative fluoroscopic image;
 a dose regulation unit for carrying out an image-based dose regulation, said dose regulation unit is embodied to optimize a dose regulation for a selected relevant image region, the image-based dose regulation being optimized by a different weighting of various image sections of the selected relevant image region;
 an image processing unit for carrying out image processing, said image processing unit embodied to optimize image processing for the selected relevant image region; and
 said selection unit is embodied for the selected relevant image region of the fluoroscopic image to be selected by a user of the x-ray system.

* * * * *